US011007156B2

(12) United States Patent
Bartholomaeus et al.

(10) Patent No.: US 11,007,156 B2
(45) Date of Patent: May 18, 2021

(54) PROLONGED RELEASE PHARMACEUTICAL COMPOSITION CONTAINING 3-(3-DIMETHYLAMINO-1-ETHYL-2-METHYL-PROPYL)PHENOL

(71) Applicant: GRUENENTHAL GMBH, Aachen (DE)

(72) Inventors: Johannes Bartholomaeus, Aachen (DE); Iris Ziegler, Rott-Roetgen (DE)

(73) Assignee: GRUENENTHAL GMBH, Aachen (DE)

( * ) Notice: Subject to any disclaimer, the term of this patent is extended or adjusted under 35 U.S.C. 154(b) by 0 days.

(21) Appl. No.: 16/600,974

(22) Filed: Oct. 14, 2019

(65) Prior Publication Data

US 2020/0038344 A1 Feb. 6, 2020

Related U.S. Application Data

(63) Continuation of application No. 15/943,175, filed on Apr. 2, 2018, now abandoned, which is a continuation of application No. 15/377,628, filed on Dec. 13, 2016, now abandoned, which is a continuation of application No. 15/018,529, filed on Feb. 8, 2016, now abandoned, which is a continuation of application No. 13/868,635, filed on Apr. 23, 2013, now abandoned, which is a continuation of application No. 13/242,800, filed on Sep. 23, 2011, now abandoned, which is a continuation of application No. 10/831,368, filed on Apr. 26, 2004, now abandoned, which is a continuation of application No. PCT/EP02/11809, filed on Oct. 22, 2002, now abandoned.

(30) Foreign Application Priority Data

Oct. 24, 2001 (DE) .................................. 10152469.2
Oct. 16, 2002 (DE) .................................. 10248309.4

(51) Int. Cl.
| | |
|---|---|
| *A61K 9/20* | (2006.01) |
| *A61K 31/137* | (2006.01) |
| *A61K 9/50* | (2006.01) |
| *A61K 31/135* | (2006.01) |
| *A61K 31/136* | (2006.01) |
| *A61K 9/00* | (2006.01) |

(52) U.S. Cl.
CPC .......... *A61K 31/137* (2013.01); *A61K 9/0053* (2013.01); *A61K 9/2054* (2013.01); *A61K 9/5047* (2013.01); *A61K 31/135* (2013.01); *A61K 31/136* (2013.01)

(58) Field of Classification Search
None
See application file for complete search history.

(56) References Cited

U.S. PATENT DOCUMENTS

| | | |
|---|---|---|
| 3,870,790 A | 3/1975 | Lowey et al. |
| 4,126,672 A | 11/1978 | Sheth et al. |
| 4,389,393 A | 6/1983 | Schor et al. |
| 4,612,008 A | 9/1986 | Wong et al. |
| 4,765,989 A | 8/1988 | Wong et al. |
| 4,783,337 A | 11/1988 | Wong et al. |
| 4,844,909 A | 7/1989 | Goldie et al. |
| 5,126,145 A | 6/1992 | Evenstad et al. |
| 5,266,331 A | 11/1993 | Oshlack et al. |
| 5,286,493 A | 2/1994 | Oshlack et al. |

(Continued)

FOREIGN PATENT DOCUMENTS

| | | |
|---|---|---|
| DE | 2117239 A | 10/1983 |
| DE | 3309516 A1 | 12/1983 |

(Continued)

OTHER PUBLICATIONS

B. Huet De Barochez et al., Oral Sustained Release Dosage Dorms Comparison Between Matrices and Reservoir Devices, Drug Development and Industrial Pharmacy, vol. 15, Nos. 6 and 7, 1989, pp. 1001-1020.

(Continued)

*Primary Examiner* — Susan T Tran

(74) *Attorney, Agent, or Firm* — Norris McLaughlin, P.A.

(57) ABSTRACT

A pharmaceutical formulation for prolonged release of the active ingredient 3-(3-dimethylamino-1-ethyl-2-methylpropyl)phenol or a pharmaceutically acceptable salt thereof in a matrix containing between 1 and 80 wt. % of at least one pharmaceutically acceptable hydrophilic or hydrophobic polymer as a matrix forming agent and exhibiting in vivo the following release rate: 3 to 35% by weight (based on 100% by weight active ingredient) 3-(3-dimethylamino-1-ethyl-2-methyl-propyl)phenol released after 0.5 hours; 5 to 50% by weight 3-(3-dimethylamino-1-ethyl-2-methyl-propyl)phenol released after 1 hour; 10 to 75% by weight 3-(3-dimethylamino-1-ethyl-2-methyl-propyl)phenol released after 2 hours; 15 to 82% by weight 3-(3-dimethylamino-1-ethyl-2-methyl-propyl)phenol released after 3 hours; 30 to 97% by weight 3-(3-dimethylaminol-1-ethyl-2-methyl-propyl)phenol released after 6 hours; more than 50% by weight 3-(3-dimethylamino-1-ethyl-2-methyl-propyl)phenol released after 12 hours; more than 70% by weight 3-(3-dimethylamino-1-ethyl-2-methyl-propyl)phenol released after 18 hours, and more than 80% by weight 3-(3-dimethylamino-1-ethyl-2-methyl-propyl)phenol released after 24 hours.

26 Claims, 1 Drawing Sheet

(56) References Cited

U.S. PATENT DOCUMENTS

| | | |
|---|---|---|
| 5,478,577 A | 12/1995 | Sackler et al. |
| 5,591,452 A | 1/1997 | Miller et al. |
| 5,601,842 A * | 2/1997 | Bartholomaeus .... A61K 31/135 424/464 |
| 5,601,984 A | 2/1997 | Kohne |
| 5,672,360 A | 9/1997 | Sackler et al. |
| 5,733,936 A | 3/1998 | Buschmann et al. |
| 5,741,524 A | 4/1998 | Staniforth et al. |
| 5,811,582 A | 9/1998 | Buschmann et al. |
| 5,843,480 A | 12/1998 | Miller et al. |
| 5,891,471 A | 4/1999 | Miller et al. |
| 5,955,104 A | 9/1999 | Momberger et al. |
| 6,096,339 A | 8/2000 | Ayer et al. |
| 6,143,322 A | 11/2000 | Sackler et al. |
| 6,177,102 B1 | 1/2001 | Chen et al. |
| 6,245,357 B1 | 6/2001 | Edgren et al. |
| 6,248,737 B1 * | 6/2001 | Buschmann .......... C07C 215/30 514/114 |
| 6,254,887 B1 | 7/2001 | Miller et al. |
| 6,340,475 B2 | 1/2002 | Shell et al. |
| 6,436,441 B1 | 8/2002 | Sako et al. |
| 6,689,386 B2 | 2/2004 | Baichwal |

FOREIGN PATENT DOCUMENTS

| | | |
|---|---|---|
| DE | 3625458 A1 | 2/1987 |
| DE | 4329794 A1 | 3/1995 |
| DE | 4426245 A1 | 2/1996 |
| DE | 69400215 T2 | 10/1996 |
| DE | 19630035 A1 | 1/1998 |
| DE | 19901683 A1 | 7/2000 |
| DE | 10109763 A1 | 9/2002 |
| DE | 102483094 A1 | 4/2004 |
| EP | 0624366 A1 | 11/1994 |
| EP | 0 642 788 A2 | 3/1995 |
| EP | 0 753 506 A1 | 1/1997 |
| EP | 0693475 B1 | 2/1998 |
| EP | 0983995 A2 | 3/2000 |
| WO | WO 95/14480 | 6/1995 |

OTHER PUBLICATIONS

D.A. Alderman, A Review of Cellulose Ethers in Hydrophelic matrices for Oral Controlled Release Dosage Forms, Int. J. Pharma Tech & Prod. Mfr., 1984, 9 pages.

Ford et al., Importance of Drug Type, Tablet Shape and Added Diluents on Drug Release Kinetics from Hydroxypropylmethylcellulose Matrix Tablets, Int. J. Pharma., 1987, 12 pages.

Formulating for Controlled Release with Methocel Premium Cellulos Ethers, the Dow Chemical Company, 1987, 25 pages.

Howard C. Ansel et al., Pharmaceutical Dosage Forms and Drug Deliver Systems, 7th Edition, Modified-Release Dosage Forms and Drug Delivery Systems, 1999 (five (5) pages).

Six-Month Implementation Guide, U.S. Pharmacopoeia, National Formulary, Chapter 711-Dissolution, Physical Tests/(711) Dissolution, Copyright 2010, 9 pages.

Zhichao et al. "Effects of properties of Hydroxypropylmethylcellulose on the Dissoulution of Drugs from Hydrophilic Matrix tablets"; Acta Pharmaceutica Sinica 1994 29(12) pp. 920-924.

Raffa et al.; "Mechanistic and functional differentiation of tapentadol and tramadol"; Exp Opin Pharmacother. 2012.

Pharmeuropa 2000_12(2)_p333-335.

Hu Wen-Duo <Clinical Guidelines of National Essential & New Special Drugs>, Sep. 1996, 1st edition, p291 (CN; EN translation).

* cited by examiner

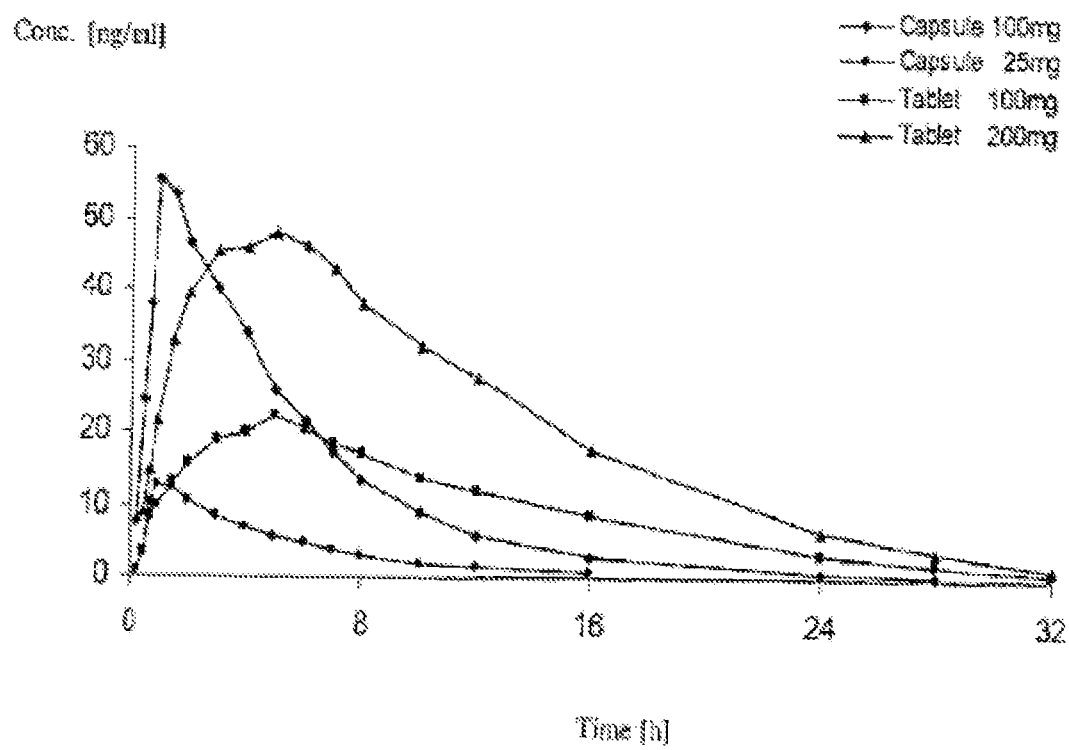

PROLONGED RELEASE PHARMACEUTICAL COMPOSITION CONTAINING 3-(3-DIMETHYLAMINO-1-ETHYL-2-METHYL-PROPYL)PHENOL

CROSS REFERENCE TO RELATED APPLICATIONS

This application is a continuation of application Ser. No. 15/943,175, filed Apr. 2, 2018, which is a continuation of application Ser. No. 15/377,628, filed Dec. 13, 2016, now abandoned, which is a continuation of application Ser. No. 15/018,529, filed Feb. 8, 2016, now abandoned, which is a continuation of application Ser. No. 13/868,635, filed Apr. 23, 2013, now abandoned, which is a continuation of application Ser. No. 13/242,800, filed Sep. 23, 2011, now abandoned, which in turn was a continuation of co-pending application Ser. No. 10/831,368, filed Apr. 26, 2004, now abandoned, which in turn was a continuation of international patent application no. PCT/EP02/11809, filed Oct. 22, 2002, designating the United States of America, and published in German as WO 03/035053, the entire disclosure of which is incorporated herein by reference. Priority is claimed based on Federal Republic of Germany patent application nos. DE 101 52 469.2, filed Oct. 24, 2001, and DE 102 48 309.4, filed Oct. 16, 2002.

BACKGROUND OF THE INVENTION

The present invention relates to a slow-release pharmaceutical formulation, containing 3-(3-dimethylamino-1-ethyl-2-methyl-propyl)phenol or a pharmaceutically acceptable salt thereof in a matrix.

3-(3-dimethylamino-1-ethyl-2-methyl-propyl)phenol is known from European patent no. EP 693,475 as an analgesic pharmaceutical composition and can be administered orally. Conventional formulations for oral administration of 3-(3-dimethylamino-1-ethyl-2-methyl-propyl)phenol lead to rapid release of the active ingredient in the gastrointestinal tract, so its analgesic action begins rapidly. At the same time, a rapid reduction in the action is observed. Therefore, the treatment of pronounced chronic pain with 3-(3-dimethylamino-1-ethyl-2-methyl-propyl)phenol formerly required administration of the pharmaceutical composition at relatively short intervals, for example four to eight times daily, to ensure an adequately high concentration of active ingredient in the patient's blood plasma. However, the need for frequent dosing easily leads to errors in administration and to undesirable variations in concentration in the plasma which are detrimental to patient compliance and the therapeutic benefit, particularly when treating chronically painful conditions. It is therefore desirable to have a slow release pharmaceutical composition (retard formulation) for oral administration of the active ingredient, 3-(3-dimethylamino-1-ethyl-2-methyl-propyl)phenol.

In the prior art, retard formulations are generally known for a large number of different active ingredients. Conventional forms of retardation include coating retardation and matrix retardation.

In coating retardation as described, for example, in published German patent application no. DE 36 25 458, the nucleus of a pharmaceutical composition containing an active ingredient is provided with a coating which consists of one or more hydrophilic and/or hydrophobic polymers and slows down release of the active ingredient.

In matrix retardation, the active ingredient is contained in a matrix which is formed from one or more excipients and controls release of the active ingredient. Published German patent application no. DE 33 09 516, for example, accordingly discloses a process for producing matrix formulations with hydroxypropylmethyl cellulose (HPMC) as excipient and slow release, in part, of the active ingredient, the excipient making up not more than one third of the weight of the formulation and consisting of at least one hydroxypropylmethyl cellulose having a methoxy content of 16 to 24% by weight, a hydroxypropyl content of 4 to 32% by weight and a numerically averaged molecular weight of at least 50,000. The formulations disclosed in DE 33 09 516 A1 contain HPMCs having viscosities (in a 2% by weight aqueous solution at 20° C.) between 15 and 30,000 cPs (15 to 30,000 mPa·s). Release behavior which is independent of the pH of the dissolution medium is not disclosed in DE 33 09 516 A1.

SUMMARY OF THE INVENTION

Accordingly, it is an object of the present invention to provide a pharmaceutical formulation which achieves slow release of 3-(3-dimethylamino-1-ethyl-2-methyl-propyl)phenol.

This object and other objects are achieved in accordance with the present invention by a slow-release pharmaceutical formulation containing 3-(3-dimethylamino-1-ethyl-2-methyl-propyl)phenol or a pharmaceutically acceptable salt thereof in a matrix with slow release of active ingredient, in which the matrix contains 1 to 80% by weight, preferably 5 to 80% by weight, of one or more hydrophilic or hydrophobic polymers as pharmaceutically acceptable matrix forming agents and has the following release rate in vitro, measured by the Ph. Eur. Paddle Method at 75 rpm in a buffer (to Ph. Eur.) at a pH of 6.8 at 37° C. and detected using a UV spectrometer:

3 to 35% by weight (based on 100% by weight active ingredient) of 3-(3-dimethylamino-1-ethyl-2-methyl-propyl)phenol released after 0.5 hours;
5 to 50% by weight of 3-(3-dimethylamino-1-ethyl-2-methyl-propyl)phenol released after 1 hour;
10 to 75% by weight of 3-(3-dimethylamino-1-ethyl-2-methyl-propyl)phenol released after 2 hours;
15 to 82% by weight of 3-(3-dimethylamino-1-ethyl-2-methyl-propyl)phenol released after 3 hours;
30 to 97% by weight of 3-(3-dimethylamino-1-ethyl-2-methyl-propyl)phenol released after 6 hours;
more than 50% by weight of 3-(3-dimethylamino-1-ethyl-2-methyl-propyl)phenol released after 12 hours;
more than 70% by weight of 3-(3-dimethylamino-1-ethyl-2-methyl-propyl)phenol released after 18 hours, and
more than 80% by weight of 3-(3-dimethylamino-1-ethyl-2-methyl-propyl)phenol released after 24 hours.

It has surprisingly been found that the formulation according to the invention releases the active ingredient, 3-(3-dimethyl amino-1-ethyl-2-methylpropyl)phenol, slowly when administered orally and is therefore suitable for administration at intervals of at least 12 hours. The formulation according to the invention therefore enables pain therapy, during which the analgesic, 3-(3-dimethylamino-1-ethyl-2-methyl-propyl)phenol, only has to be administered once daily, for example at 24 hour intervals, or twice daily, preferably at 12 hourly intervals, in order to ensure an adequate concentration of the active ingredient in the plasma. A corresponding duration of efficacy and the maintenance of an adequate level in the blood plasma are demonstrated by simulation studies and experimental investigations.

It is particularly surprising that the formulation according to the invention not only ensures long-lasting therapeutic efficacy over a relatively long period (at least 12 hours) due to the slow release of the active ingredient, but at the same time allows the active ingredient to start flowing rapidly in the plasma when the pharmaceutical composition is first administered, leading to a rapid onset of pain relief in the patient. Therefore, the pain suffered by a patient can rapidly be alleviated when the formulation according to the invention is administered without the analgesic action quickly fading again. The formulation according to the invention therefore combines properties of a formulation with immediate release of active ingredient—rapid pain relief due to adequately high concentration of active ingredient just after administration of the pharmaceutical composition with properties of a formulation having slow release—long-lasting analgesic action due to maintenance of an adequately high level of active ingredient over a prolonged time. By taking the analgesic in the formulation according to the invention, the patient can effectively combat his pain acutely and, at the same time, treat it effectively over a prolonged period without further measures and merely by regular administration at 12 (or 24) hourly intervals.

The active ingredient of the formulation according to the invention is contained in a slow release matrix. It is also conceivable, however, that the active ingredient be contained in a matrix with conventional release behavior and the slow release be achieved by a retarding coating.

In a further possibility the slow release behavior is achieved by an osmotically driven release system.

If the formulation according to the invention contains a slow release matrix, the matrix contains 1 to 80% by weight of one or more hydrophilic or hydrophobic polymers as pharmaceutically acceptable matrix forming agents, for example rubbers, cellulose ethers, cellulose esters, acrylic resins, materials derived from proteins, fats, waxes, fatty alcohols or fatty acid esters. When using hydrophilic polymers as matrix forming agents, it is preferable for the matrix to comprise 5 to 80% by weight matrix forming agents.

The present invention also relates to a pharmaceutical formulation which contains 3-(3-dimethylamino-1-ethyl-2-methyl-propyl)phenol or a pharmaceutically acceptable salt thereof in a matrix with slow release of active ingredient, in which the matrix contains 1 to 80% by weight, in particular 5 to 80 by weight, of one or more hydrophilic or hydrophobic polymers as pharmaceutically acceptable matrix forming agents and which comprise cellulose ethers and/or cellulose esters having a viscosity (determined using a Pharm. Eu. capillary viscosimeter) of 3,000 to 150,000 mPa·s in a 2% by weight aqueous solution at 20° C. as pharmaceutically acceptable matrix forming agents. These compositions have the above-mentioned release profile according to the invention.

Preferred pharmaceutically acceptable matrix forming agents include cellulose ethers and/or cellulose esters having a viscosity between 10,000, in particular 50,000 mPa·s, and 150,000 mPa·s in a 2% by weight aqueous solution at 20° C.

Particularly suitable pharmaceutically acceptable matrix forming agents may be selected from the group consisting of hydroxypropylmethyl celluloses (HPMC), hydroxyethyl celluloses, hydroxypropyl celluloses (HPC), methyl celluloses, ethyl celluloses and carboxymethyl celluloses and are selected, in particular, from the group consisting of HPMCs, hydroxyethyl celluloses and HPCs. HPMCs having a viscosity of approx. 100,000 mPa·s, measured in a 2% by weight aqueous solution at 20° C. are most preferred.

The active ingredient, 3-(3-dimethylamino-1-ethyl-2-methyl-propyl)phenol, exists as such, i.e. as a free base, but also in the form of pharmaceutically acceptable salts, for example as a hydrochloride. Preparation of the free base is known from published European patent application no. EP 693,475. Where EP 693,475 does not also disclose the preparation of pharmaceutically acceptable salts such as hydrochloride, these may be obtained from the free base by processes generally known in the art.

3-(3-dimethylamino-1-ethyl-2-methyl-propyl)phenol has two asymmetric centers, so the compound can exist in the form of four different stereoisomers. In the formulation according to the invention 3-(3-dimethylamino-1-ethyl-2-methyl-propyl)phenol can exist as a mixture of all four diastereomers in any ratio, but also as a mixture of two or three of the four stereoisomers or in pure stereoisomer form. Preferred stereoisomers include (+)-(1S,2S)-3-(3-dimethyl-amino-1-ethyl-2-methyl-propyl)phenol and (−)-(1R,2R)-3-(3-dimethylamino-1-ethyl-2-methyl-propyl)phenol, which, in the formulation according to the invention, can exist as a mixture, in particular as a 1:1 mixture (racemate) or particularly preferably in pure isomer form. For the purposes of the present invention, therefore, the term "active ingredient" denotes 3-(3-dimethylamino-1-ethyl-2-methyl-propyl)phenol as a mixture of various stereoisomers thereof or as one pure stereoisomer thereof as a free base or in the form of a pharmaceutically acceptable salt respectively.

In the pharmaceutical compositions according to the invention, the slow release active ingredient content is preferably between 0.5 and 85% by weight and the content of pharmaceutically acceptable matrix forming agents between 8 and 40% by weight. Particularly preferred pharmaceutical compositions have a slow release active ingredient content between 3 and 70% by weight, in particular between 8 and 66% by weight, and a content of pharmaceutically acceptable matrix forming agents between 10 and 35% by weight, in particular between 10 and 30% by weight. If enantiomerically pure (+)-(1 S,2S)-3-(3-dimethylamino-1-ethyl-2-methyl-propyl)phenol (or a mixture of the (+) and (−) enantiomers with a large excess of the (+) enantiomer) is used as active ingredient, it is particularly preferred if the active ingredient content lies at the lower limit, i.e. between 0.5 and 25% by weight (based on the total weight). If enantiomerically pure (−)-(1R,2R)-3-(3-dimethylamino-1-ethyl-2-methyl-propyl)phenol (or a mixture of the (+) and (−) enantiomers with a large excess of the (−) enantiomer) is used as active ingredient, it is particularly preferred if the active ingredient content lies between 16 and 66% by weight.

Further components of the matrix of the formulation according to the invention may optionally include digestible long-chain (i.e. with 8 to 50 carbon atoms, preferably 12 to 50 carbon atoms) unsubstituted or substituted hydrocarbons such as fatty alcohols, fatty acid glyceryl esters, mineral and vegetable oils as well as waxes. Hydrocarbons having a melting point between 25° and 90° C. are preferred. Fatty alcohols are particularly preferred and lauryl alcohol, myristyl alcohol, stearyl alcohol, cetyl alcohol and cetylstearyl alcohol are more particularly preferred. Their content in the matrix may be 0 to 60% by weight. The matrix can alternatively or additionally contain polyethylene glycols in a content of 0 to 60% by weight.

The pharmaceutical formulations according to the invention can also contain, as further components, pharmaceutically acceptable auxiliaries such as fillers, for example lactose, microcrystalline cellulose (MCC) or calcium hydrogen phosphate as well as glidants, lubricants and flow regulators such as talcum, magnesium stearate, stearic acid and/or highly dispersed silicon dioxide, of which the total content in the tablet may be between 0 and 80% by weight, preferably between 5 and 65% by weight.

The release rate of an active ingredient from an administrable form frequently depends on the pH of the release medium. This can vary in a pH range from less than 1 to about 8 as the pharmaceutical composition passes through the gastrointestinal tract. These variations also can vary from one person to another. One and the same person can also have a different pH/time profile during passage through the gastrointestinal tract from one administration to another. Thus, if the release rate of the active ingredient from the pharmaceutical composition is dependent on the pH, this can lead to different release rates in vivo and therefore different biocompatibility.

Surprisingly, however, the release profiles of the active ingredient (either in the form of the base or of a pharmaceutically acceptable salt thereof) from a pharmaceutical formulation according to the invention are independent of the pH which can occur physiologically during passage through the gastrointestinal tract. The release profiles with an ambient pH of 1.2, 4.0 and 6.8 are identical to one another and also in comparison to the release during a pH/time profile from pH 1.2 via pH 2.3 and pH 6.8 to pH 7.2.

It has been found that it is immaterial for achieving the slow release of active ingredient from the formulation according to the invention, which preferably exists in tablet form, whether a water-soluble filler, for example lactose, an insoluble filler which does not swell in an aqueous medium, for example calcium hydrogen phosphate, or an insoluble filler which swells in an aqueous medium, for example microcrystalline cellulose, is used as filler with otherwise unchanged values and unchanged composition of the tablet, based on the active ingredient, the matrix forming agent and the optional components. All these pharmaceutical compositions exhibit a corresponding release behavior.

It is also surprising that, in the compositions according to the invention with a given amount of active ingredient, the quantity of matrix forming agent and the quantity of optional components can each vary over a relatively large range without affecting the therapeutic efficacy of at least 12 hours or with twice daily administration (providing that the above-mentioned limits on the quantity of active ingredient, matrix forming agent and further optional components are adhered to). Efficacy over at least 12 hours is assured, for example, with an active ingredient content of approx. 32.25% by weight (based on the weight of the total composition) in a composition of approx. 12.9% by weight HPMC having a viscosity of 100,000 mPa·s as matrix forming agent and a content of approx. 52.6% by weight of, for example, MCC as filler and also in a composition of approx. 25.8% by weight of the same HPMC and approx. 39.7% by weight MCC (or lactose monohydrate) with otherwise identical amounts of glidant, lubricant and flow regulators. The same applies to compositions according to the invention with a higher or lower active ingredient content within the specified limits.

It has also extremely surprisingly been found that, when the pharmaceutical formulations according to the invention with slow release of the active ingredient are administered to human volunteers, a biocompatibility which is the same as in formulations with immediate release of active ingredients is unexpectedly achieved despite the high first-pass effect for the active ingredient.

Compositions according to the invention which have a $t_{max}$ value in the in vivo plasma concentration/time graph of between 2 and 10 hours, in particular between 3.5 and 6 hours and more particularly preferably between 4 and 5.5 hours after oral administration of the composition, i.e. compositions which yield peak plasma levels during said periods, are also preferred.

As active ingredient, the formulation according to the invention contains 3-(3-dimethylamino-1-ethyl-2-methyl-propyl)phenol as such and/or as a pharmaceutically acceptable salt in an amount typically of 2.5 to 800 mg, in particular 5 to 400 mg, more particularly preferably 10 to 250 mg (weight of the active ingredient 3-(3-dimethyl-amino-1-ethyl-2-methyl-propyl)phenol as hydrochloride) per dose unit. The release behavior of the formulation according to the invention is not affected by the exact amount of the active ingredient provided that the above-mentioned limits are adhered to. Due to the different active strength of the two particularly preferred enantiomers (+)-(1S,2S)-3-(3-dimethylamino-1-ethyl-2-methyl-propyl)phenol and (−)-(1R,2R)-3-(3-dimethylamino-1-ethyl-2-methyl-propyl)phenol, it is preferred if the stronger (±)-(1S,2S)-3-(3-dimethylamino-1-ethyl-2-methyl-propyl)phenol exists in an amount of 2.5 to 80 mg, in particular 5 to 40 mg and more particularly preferably in an amount of 10 to 25 mg active ingredient (based on the hydrochloride) in the formulations according to the invention, while the (−)-(1R,2R)-3-(3-dimethylamino-1-ethyl-2-methyl-propyl)phenol preferably is present in an amount of 25 to 800 mg, in particular 50 to 400 mg and more particularly preferably in an amount of 100 to 250 mg active ingredient (based on the hydrochloride) in the formulations according to the invention, more specifically on condition that the above-mentioned limits are adhered to.

Within the scope of this invention, the term "pharmaceutically acceptable salt" of the active ingredient refers to a salt of the active ingredient which is physiologically acceptable for pharmaceutical use, in particular when administered to mammals and/or humans. Pharmaceutically acceptable salts of this type may be formed, for example, with inorganic or organic acids.

The pharmaceutical formulations according to the invention can exist both as a simple tablet and as a coated tablet, for example as a film tablet or dragee. The tablets are typically round and biconvex, but oblong tablet shapes which allow the tablet to be divided are also possible. Granules, spheroids, pellets or microcapsules which are poured into sachets or capsules or may be compressed to disintegrating tablets are also possible within the scope of the invention.

One or more coating layers may be used for the coated tablets. Suitable coating materials include known hydroxypropylmethyl celluloses having a low viscosity of approx. 1 to 100 mPa·s and a low molecular weight of <10,000 (for example Pharmacoat 606 with a viscosity of 6 mPa·s in a 2% by weight aqueous solution at 20° C.), which only slightly influence the release profile of the pharmaceutical compositions according to the invention. Diffusion coatings known to persons skilled in the art and based, for example, on swellable but water-insoluble poly(meth)acrylates lead to modulation of the slow release of the active ingredients from pharmaceutical formulations according to the invention. The tablet core which contains the active ingredient, releases the active ingredient slowly and has an active ingredient content preferably between 0.5 and 85% by weight, particularly preferably between 3 and 70% by weight and more particularly preferably between 8 and 66% by weight. The tablet core can be sheathed with additional active ingredient which is released as an initial dose without retardation by various processes known to persons skilled in the art, for example dragee production, spraying from solutions or suspensions or by application of powder, but without this being absolutely essential for the desired slow release with a simultaneous rapid initial flow of the active ingredient for rapid pain relief on first administration of the pharmaceutical formulation according to the invention. Multilayered and shell-type tablets represent further embodiments, in which 3-(3-dimethylamino-1-ethyl-2-methyl-propyl)phenol or a pharmaceutically acceptable salt thereof is released slowly in one or more layers of the multilayer tablet with an active ingredient content preferably between 0.5 and 85% by weight, particularly preferably between 3 and 70% by weight, and more particularly preferably between 8 and 66% by weight, or in the core of the shell-type tablet with an active ingredient content preferably between 0.5 and 85% by weight, particularly preferably between 3 and 70% by weight, and more particularly preferably between 8 and 66% by weight by a pharmaceutically acceptable matrix forming agent, and the release of the active ingredient takes place without retardation in one or more layers of the multilayer tablet or the outer shell layer of the shell-type tablets. Multilayer and shell-type tablets can contain one or more coatings which are free from active ingredients.

Instead of a slow release matrix in the slow release pharmaceutical formulation, it is also possible to use a normal release matrix with a coating which retards release of the active ingredient. For example, the active ingredient can be contained in a conventional matrix of microcrystalline cellulose and optionally further pharmaceutical auxiliaries such as binders, fillers, glidants, lubricants and flow regulators, which are covered or coated with a material controlling the slow release of the active ingredient in an aqueous medium. Suitable coating agents include, for example, water-insoluble waxes and polymers such as polymethacrylates (Eudragit or the like) or water-insoluble celluloses, in particular ethyl cellulose. The coating material can optionally also contain water-soluble polymers such as polyvinyl pyrrolidone, water-soluble celluloses such as hydroxypropylmethyl cellulose or hydroxypropyl cellulose, other water-soluble agents such as Polysorbate 80 or hydrophilic pore-forming agents such as polyethylene glycol, lactose or mannitol.

As an alternative or a supplement to the possibilities of a slow release matrix in the prolonged release pharmaceutical formulation or of a normal release matrix with a coating which retards the release of the active ingredient, an osmotically driven release system can also be used to achieve a slow release. With a release system of this type, preferably an oral system, at least one, preferably all, surface(s) of the release system, preferably those which are in contact or which may come into contact with the release medium, are semi-permeable, preferably provided with a semi-permeable coating, so the surfaces are permeable to the release medium but substantially, and preferably completely, impermeable to the active ingredient, whereby the surface and/or optionally the coating comprises at least one opening for releasing the active ingredient. The active ingredient 3-(3-dimethylamino-1-ethyl-2-methyl-propyl)phenol or a pharmaceutically acceptable salt thereof, preferably (+)-(1 S,2S)-3-(3-dimethylamino-1-ethyl-2-methyl-propyl)phenol or a pharmaceutically acceptable salt thereof and/or (−)¬(1R, 2R)-3-(3-dimethylamino-1-ethyl-2-methyl-propyl)phenol or a pharmaceutically acceptable salt thereof or a mixture thereof can, but does not have to, be present in a matrix. This is preferably taken to mean a system in tablet form with a delivery opening, an osmotic pharmaceutical composition core, a semi-permeable membrane and a polymeric part which exerts pressure. A useful example of such a system is the OROS® system from ALZA Corporation, USA, details of which are available on the Alza Corporation internet site and/or in product literature of Alza Corporation. These include in particular the OROS® Push-Pull™ system, the OROS® Delayed Push-Pull' system, the OROS® Multi-Layer Push-Pul1™ system, the OROS® Push-Stick System and in certain cases the L-OROS™. Embodiments and examples of the actual production of osmotically driven release systems can be found in U.S. Pat. Nos. 4,765,989; 4,783,337 and 4,612,008, the complete disclosures of which are incorporated herein by reference.

The compositions according to the invention may be produced, for example, by the following general processes: weighed amounts of the components of the composition (active ingredient, matrix forming agent and optional components) successively introduced and then screened on a conventional screening machine, for example a Quadro Comil U10 screening machine using, for example, a conventional screen size of approx. 0.813 mm. The screened material is then mixed in a container mixer, for example a Bohle container mixer. Typical mixer operating conditions are: duration approx. 15 min+45 seconds at a speed of 20±1 rpm. The resulting powder mixture is subsequently compressed to a tablet on a tablet press, for example a Korsch EKO tablet press with a round die curved in the form of a dragee having a diameter of 10 mm. Alternatively, the powder mixture can be compacted and the compacts subsequently screened (Comill 3 mm friction macerating sieve and subsequent 1.2 mm round hole screen), the resulting granules then being compressed in the above-described manner with addition of lubricant (for example magnesium stearate) for example on an EKO tablet press with 10 mm round dies. Granulation can also be carried out by wet granulation using aqueous or organic solvents. Aqueous solvents with or without a suitable binder are preferred. The production process can readily be adapted to the respective requirements and the desired form of administration by procedures well known to persons skilled in the art.

The production of pharmaceutical formulations according to the invention is characterized by high repeatability of the release properties of the resulting compositions containing 3-(3-dimethylamino-1-ethyl-2-methyl-propyl)phenol or a pharmaceutically acceptable salt thereof. The release profile of pharmaceutical compositions according to the invention has proven to be stable for a storage time of at least one year under conventional storage conditions according to ICH Q1AR Stability Testing Guidelines.

With once or twice daily administration of a pharmaceutical formulation according to the invention by the patient, good therapeutic efficacy is reliably achieved in the case of continuously strong pain.

BRIEF DESCRIPTION OF THE DRAWING

FIG. 1 is a graph of average serum concentrations achieved by differing pharmaceutical formulations in a clinical trial.

EXAMPLES

The following examples serve to illustrate the present invention and preferred embodiments, but do not restrict its scope.

Example 1

A batch of 1,000 matrix tablets was produced as described below having with the following composition per tablet:

| | |
|---|---|
| (−)-(1R,2R)3-(3-dimethyl amino-1-ethyl-2-methyl-propyl)phenol hydrochloride | 100 mg |
| Hydroxypropylmethyl cellulose (Metolose 90 SH 100,000 from Shinetsu, 100,000 mPa · s | 80 mg |
| Microcrystalline cellulose (Avicel PH 102 from FMC) | 123 mg |
| Highly dispersed silicon dioxide | 4 mg |
| Magnesium stearate | 3 mg |
| Total amount | 310 mg |

All components were weighed in and screened on a Quadro Comil U10 screening machine using a screen size of 0.813 mm, mixed in a container mixer (Bohle LM 40) for 15 minutes±15 seconds at a speed of 20±1 rpm and pressed on a Korsch EKO eccentric press to tablets curved in the manner of dragees with a diameter of 10 mm, a radius of curvature of 8 mm and an average tablet weight of 310 mg. The in vitro release was determined by the Ph. Eur. Paddle Method at 75 rpm in 900 ml pH 6.8 buffer according to Ph. Eur. at 37° C. and with detection using a UV spectrometer, and is reproduced in the following table:

| Time (min) | Total amount of active ingredient released [%] |
|---|---|
| 0 | 0 |
| 30 | 18 |
| 60 | 27 |
| 120 | 41 |
| 180 | 50 |
| 240 | 59 |
| 360 | 71 |
| 480 | 80 |
| 600 | 87 |
| 720 | 93 |

Example 2

Using a process similar to that described in Example 1, 3,000 matrix tablets were produced having the following composition per tablet:

| | |
|---|---|
| (−)-(1R,2R)3-(3-dimethylamino-1-ethyl-2-methyl-propyl)phenol hydrochloride | 200 mg |
| Hydroxypropylmethyl cellulose (Metolose 90 SH 100,000 from Shinetsu, 100,000 mPa · s | 80 mg |
| Microcrystalline cellulose (Avicel PH 102 from FMC) | 23 mg |
| Highly dispersed silicon dioxide | 4 mg |
| Magnesium stearate | 3 mg |
| Total amount | 310 mg |

The in vitro release was determined as in Example 1.

| Time (min) | Total amount of active ingredient released [%] |
|---|---|
| 0 | 0 |
| 30 | 19 |
| 60 | 30 |
| 120 | 46 |
| 180 | 58 |
| 240 | 68 |
| 360 | 84 |
| 480 | 93 |
| 720 | 99 |

Example 3

Using a process similar to that described in Example 1, a batch of 3,000 matrix tablets were produced having the following composition per tablet:

| | |
|---|---|
| (−)-(1R,2R)3-(3-dimethylamino-1-ethyl-2-methyl-propyl)phenol hydrochloride | 100 mg |
| Hydroxypropylmethyl cellulose (Metolose 90 SH 100,000 from Shinetsu, 100,000 mPa · s | 40 mg |
| Microcrystalline cellulose (Avicel PH 102 from FMC) | 163 mg |
| Highly dispersed silicon dioxide | 4 mg |
| Magnesium stearate | 3 mg |
| Total amount | 310 mg |

The in vitro release was determined as in Example 1. In addition, the release was determined under otherwise identical conditions at stirring speeds of 50 and 100 rpm.

| Time (min) | Total amount of active ingredient released [%] at 50 rpm | Total amount of active ingredient released [%] at 75 rpm | Total amount of active ingredient released [%] at 100 rpm |
|---|---|---|---|
| 0 | 0 | 0 | 0 |
| 30 | 20 | 20 | 21 |
| 60 | 35 | 33 | 35 |
| 120 | 54 | 51 | 53 |
| 180 | 67 | 63 | 66 |
| 240 | 76 | 73 | 76 |
| 360 | 89 | 87 | 89 |
| 480 | 97 | 95 | 97 |
| 600 | 100 | 100 | 100 |

Example 4

Using a process similar to that described in Example 1, a batch of 200 matrix tablets was produced having the following composition per tablet:

| | |
|---|---|
| (−)-(1R,2R)3-(3-dimethylamino-1-ethyl-2-methyl-propyl)phenol hydrochloride | 100 mg |
| Hydroxypropylmethyl cellulose (Metolose 90 SH from Shinetsu, 100,000 mPa · s | 80 mg |
| Lactose monohydrate 230 (Meggle) | 123 mg |
| Highly dispersed silicon dioxide | 4 mg |
| Magnesium stearate | 3 mg |
| Total amount | 310 mg |

The in vitro release was determined as in Example 1.

| Time (min) | Total amount of active ingredient released [%] |
|---|---|
| 0 | 0 |
| 30 | 16 |
| 60 | 26 |
| 120 | 39 |
| 180 | 49 |
| 240 | 57 |
| 360 | 71 |
| 480 | 81 |
| 600 | 87 |
| 720 | 92 |

Example 5

Matrix tablets with the following composition per tablet

| | |
|---|---|
| (−)-(1R,2R)3-(3-dimethylamino-1-ethyl-2-methyl-propyl)phenol hydrochloride | 100 mg |
| Hydroxypropylmethyl cellulose (Metolose 90 SH 100,000 from Shinetsu, 100,000 mPa · s | 40 mg |
| Cellactose 80 (Meggle) | 163 mg |
| Highly dispersed silicon dioxide | 4 mg |
| Magnesium stearate | 3 mg |
| Total amount | 310 mg | were produced by a process similar to that described in Example 1 in a batch size of 100 tablets.

The in vitro release was determined as an Example 1.

| Time (min) | Total amount of active ingredient released [%] |
|---|---|
| 0 | 0 |
| 30 | 18 |
| 60 | 31 |
| 120 | 48 |
| 180 | 61 |
| 240 | 71 |
| 360 | 84 |
| 480 | 91 |
| 600 | 95 |
| 720 | 97 |

Example 6

Matrix tablets with the following composition per tablet

| | |
|---|---|
| (−)-(1R,2R)3-(3-dimethylamino-1-ethyl-2-methyl-propyl)phenol hydrochloride | 100 mg |
| Hydroxypropylmethyl cellulose (Metolose 90 SH 100,000 from Shinetsu, 100,000 mPa · s | 80 mg |
| Ludipress (BASF) | 123 mg |
| Highly dispersed silicon dioxide | 4 mg |
| Magnesium stearate | 3 mg |
| Total amount | 310 mg | were produced by a process similar to that described in Example 1 in a batch size of 100 tablets.

The in vitro release was determined as in Example 1.

| Time (min) | Total amount of active ingredient released [%] |
|---|---|
| 0 | 0 |
| 30 | 17 |
| 60 | 27 |
| 120 | 40 |
| 180 | 51 |
| 240 | 59 |
| 360 | 72 |
| 480 | 82 |
| 600 | 89 |
| 720 | 93 |

Example 7

Matrix tablets with the following composition per tablet

| | |
|---|---|
| (−)-(1R,2R)3-(3-dimethylamino-1-ethyl-2-methyl-propyl)phenol hydrochloride | 50 mg |
| Hydroxypropylmethyl cellulose (Metolose 90 SH 100,000 from Shinetsu, 100,000 mPa · s | 40 mg |
| Microcrystalline cellulose (Avicel PH 102 from FMC) | 163 mg |
| Lactose 200 (Meggle) | 50 mg |
| Highly dispersed silicon dioxide | 4 mg |
| Magnesium stearate | 3 mg |
| Total amount | 310 mg | were produced by a process similar to that described in Example 1 in a batch size of 200 tablets.

The in vitro release was determined as in Example 1.

| Time (min) | Total amount of active ingredient released [%] |
|---|---|
| 0 | 0 |
| 30 | 18 |
| 60 | 31 |
| 120 | 49 |
| 180 | 61 |
| 240 | 70 |
| 360 | 82 |
| 480 | 90 |
| 600 | 94 |
| 720 | 96 |

Example 8

Matrix tablets with the following composition per tablet

| | |
|---|---|
| (−)-(1R,2R)3-(3-dimethylamino-1-ethyl-2-methyl-propyl)phenol hydrochloride | 100 mg |
| Cellactose (Meggle) | 72.5 mg |
| Hydroxyethyl cellulose (Natrosol 250 HX from Herkules) | 12.5 mg |
| Cutina HR (Henkel) | 130 mg |
| Talcum | 3 mg |
| Magnesium stearate | 2 mg |
| Total amount | 320 mg | were produced as follows in a batch size of 200 tablets. The active ingredient, Cellactose, Natrosol and Cutina were mixed then heated to 80° C. in a drying oven and granulated in a Kenwood Chef kitchen mixer. The cooled granules were screened through a 1 mm screen. After blending with magnesium stearate and talcum, the granules were pressed on a EKO eccentric press (Korsch) to 6×15 mm size oblong tablets with a breaking notch.

The in vitro release was determined as in Example 1.

| Time (min) | Total amount of active ingredient released [%] |
|---|---|
| 0 | 0 |
| 30 | 28 |
| 60 | 39 |
| 120 | 56 |
| 180 | 68 |
| 240 | 80 |
| 360 | 97 |
| 390 | 99 |

Example 9

Matrix tablets with the following composition per tablet

| | |
|---|---|
| (+)-(1S,2S)3-(3-dimethylamino-1-ethyl-2-methyl-propyl)phenol hydrochloride | 10 mg |
| Hydroxypropylmethyl cellulose (Metolose 90 SH 100,000 from Shinetsu, 100,000 mPa · s | 80 mg |
| Microcrystalline cellulose (Avicel PH 102 from FMC) | 213 mg |
| Lactose 200 (Meggle) | 50 mg |
| Highly dispersed silicon dioxide | 4 mg |
| Magnesium stearate | 3 mg |
| Total amount | 310 mg | were produced by a process similar to that described in Example 1 in a batch size of 100 tablets.

The in vitro release was determined as in Example 1.

| Time (min) | Total amount of active ingredient released [%] |
|---|---|
| 0 | 0 |
| 30 | 15 |
| 60 | 24 |
| 120 | 36 |
| 180 | 44 |
| 240 | 51 |
| 360 | 61 |
| 480 | 69 |
| 600 | 75 |
| 720 | 79 |

Example 10

Matrix tablets with the following composition per tablet:

| | |
|---|---|
| (−)-(1R,2R)3-(3-dimethylamino-1-ethyl-2-methyl-propyl)phenol hydrochloride | 100 mg |
| Hydroxypropylmethyl cellulose (Metolose 90 SH 100,000 Shinetsu, 100,000 from mPa · s | 80 mg |
| Microcrystalline cellulose (Avicel PH 102 from FMC) | 63 mg |
| Highly dispersed silicon dioxide | 4 mg |
| Magnesium stearate | 3 mg |
| Total amount | 250 mg | were produced by a process similar to that described in Example 1 in a batch size of 100 tablets.

The in vitro release was determined under the following conditions:

(A) application of the Ph. Eur. Paddle Method at 75 rpm in 900 ml pH 7.2 buffer to USP 22 at 37° C. and with detection using a UV spectrometer;

(B) application of the Ph. Eur. Paddle Method at 75 rpm, a pH of 1.2 being adjusted from 0 to 30 min, a pH of 2.3 from 30 to 120 min, a pH of 6.5 from 120 to 180 min and a pH of 7.2 for the remaining test period. The table shows the results for both experimental conditions:

| Time (min) | Total amount of active ingredient released [%] under condition (A) | Total amount of active ingredient released [%] under condition (B) |
|---|---|---|
| 0 | 0 | 0 |
| 30 | 19 | 20 |
| 60 | 29 | 30 |
| 120 | 43 | 44 |
| 180 | 54 | 55 |
| 240 | 63 | 65 |
| 360 | 78 | 80 |
| 480 | 87 | 90 |
| 600 | 94 | 97 |
| 720 | 98 | 100 |

The experiment shows that the release behavior of the formulations according to the invention is independent of the pH of the release medium.

Example 11

Pellets were produced as described below having the following composition:

| | |
|---|---|
| (−)-(1R,2R)3-(3-dimethylamino-1-ethyl-2-methyl-propyl)phenol hydrochloride | 100 mg |
| Low-substituted hydroxypropyl cellulose (L-HPC LH 31 from Shinetsu) | 75 mg |
| Aquacoat (aqueous ethyl cellulose dispersion from FMC (calculated as dry substance) | 20 mg |
| Microcrystalline cellulose (Avicel PH 101 from FMC) | 75 mg |
| Dibutyl sebacate (DBS) | 4 mg |
| Tween 80 | 0.4 mg |
| Total amount | 274.4 mg |

The active ingredient, Avicel and L-HPC were mixed for 10 minutes in a planetary mixer (Kenwood K Mixer) and then granulated with water. The moist granules were extruded in a Nica extruder with a 0.8×0.8 mm matrix and then rounded for 10 min in the Nica spheronizer at 500 rpm (1 kg loading). The pellets were dried overnight in a drying oven at 50° C. and then classified into screen fractions.

Pellets measuring 0.6 to 1.0 mm (yields about 95%) were coated in the WSG (smooth GPCG1 with a Wurster insert) at incoming air temperatures of 60° C. (product temperature 40° C.) with an aqueous dispersion of Aquacoat and DBS (20%, calculated on Aquacoat solids content), so they had an increase in weight of 9.8% (based on the original weight). The dispersion was produced in accordance with the manufacturer's instructions (FMC), the DBS together with the Tween 80 being homogenized in a proportion of the water and then being added to the dilute Aquacoat dispersion. The final dispersion had a solids content of 20% by weight and was stirred for at least 3 hours. The coated pellets were dried in the WSG and tempered in the drying oven (2 hours at 60° C.). The release was tested as in Example 1, but by the basket method at 100 rpm.

| Time (min) | Total amount of active ingredient released [%] |
|---|---|
| 0 | 0 |
| 30 | 5 |
| 60 | 15 |
| 120 | 28 |
| 180 | 43 |
| 240 | 56 |
| 360 | 73 |
| 480 | 82 |
| 600 | 87 |
| 720 | 90 |

Clinical Trial

In a monocentric, open, randomized individual dose four-way crossover trial, various forms of administration of (−)-(1R,2R)-3-(3-dimethylamino-1-ethyl-2-methyl-propyl)phenol hydrochloride (active ingredient) were administered to sixteen healthy male white subjects aged from 18 to 45 years, to determine pharmacokinetic data. Data was determined experimentally by HPLC analysis. The following were administered:

"Capsule 100 mg": capsules with immediate release of the active ingredient and 100 mg of active ingredient "Capsule 25 mg": capsules with immediate release of the active ingredient and 25 mg of active ingredient "Tablet 100 mg": tablet according to Example 1 (100 mg of active ingredient)

"Tablet 200 mg": tablet according to Example 2 (200 mg of active ingredient) The capsules were white-opaque hard gelatine capsules of size 0 EL with a filling of 360 mg, which were made up as follows:

"Capsule 100 mg": 100 mg (−)-(1R,2R)-3-(3-dimethylamino-1-ethyl-2-methyl-propyl)phenol hydrochloride, 152 mg microcrystalline cellulose, 8 mg Aerosil, 20 mg magnesium stearate and 80 mg Primojel (sodium carboxymethyl starch type A from Avebe);

"Capsule 25 mg": 25 mg (−)-(1R,2R)-3-(3-dimethylamino-1-ethyl-2-methyl-propyl)phenol hydrochloride, 227 mg microcrystalline cellulose, 8 mg Aerosil, 20 mg magnesium stearate and 80 mg Primojel (sodium carboxymethyl starch type A from Avebe))

The essential pharmacokinetic data are shown in the following table and the characteristic of the experimentally determined average serum concentration in FIG. 1.

| Parameter | "Capsule 25 mg" | "Capsule 100 mg" | "Tablet 100 mg" | "Tablet 200 mg" |
|---|---|---|---|---|
| AUC [ng · h/ml] | 69 ± 14 | 318 ± 66 | 300 ± 51 | 667 ± 141 |
| Cmax [ng/ml] | 14 ± 4 | 64 ± 19 | 23 ± 5 | 51 ± 13 |
| $t_{max}$ [h] | 1.2 ± 0.4 | 1.5 ± 0.9 | 4.6 ± 1.3 | 4.8 ± 1.1 |
| MRT* [h] | 5.8 ± 0.7 | 5.9 ± 0.9 | 10.7 ± 1.5 | 10.3 ± 1.1 |
| HVD** | 3.5 ± 1.2 | 3.6 + 1.1 | 12.4 ± 2.8 | 11.9 ± 2.3 |

*MRT = "Mean Residence Time"
**HVD = "Half Value Duration"

On the one hand, a comparison of "Capsule 100 mg" and "Tablet 100 mg" immediately shows that the formulations according to the invention excellently fulfil the task of providing a pharmaceutical formulation containing a 3-(3-dimethylamino-1-ethyl-2-methyl-propyl)phenol with slow release of active ingredient. On the other hand, when "Tablet 100 mg" is compared with "Tablet 200 mg" there is also very advantageous dose proportionality in the release behavior.

However, this also shows that the two compositions according to the invention, "Tablet 100 mg" and "Tablet 200 mg" release the active ingredient in a discernible amount but more slowly at the beginning than the two formulations with immediate release; with the two retarded formulations, however, the plasma level is higher than 10 ng/ml] after only one hour and still sufficiently high after 16 hours to ensure an analgesic action. Simulation studies for "Tablet 100 mg" also showed that, with repeated administration of the pharmaceutical composition at 12 hourly intervals, serum levels are achieved which do not fall below 20 ng/ml, so good analgesic efficacy is ensured by twice daily administration. This represents great progress for the treatment, in particular of chronic painful conditions, and allows a significant improvement in patient compliance.

The foregoing description and examples have been set forth merely to illustrate the invention and are not intended to be limiting. Since modifications of the described embodiments incorporating the spirit and substance of the invention my occur to persons skilled in the art, the invention should be construed broadly to include all variations within the scope of the appended claims and equivalents thereof

What is claimed is:

1. A slow-release oral pharmaceutical formulation comprising 3-(3-dimethylamino-1-ethyl-2-methyl-propyl)phenol or a pharmaceutically acceptable salt thereof as active ingredient in a matrix, wherein the matrix comprises 1 to 40% by weight of one or more pharmaceutically acceptable matrix forming agents selected from the group consisting of hydroxypropylmethyl celluloses (HPMC), hydroxyethyl celluloses, hydroxypropyl celluloses (HPC), methyl celluloses, ethyl celluloses and carboxymethyl celluloses, wherein the oral pharmaceutical formulation has the following in vitro release rate, measured by the Ph. Eur. Paddle Method at 75 rpm in a buffer (to Ph. Eur.) at a pH of 6.8 at 37° C. and detected using a UV spectrometer:

3 to 35% by weight (based on 100% by weight active ingredient) 3-(3-dimethylamino-1-ethyl-2-methyl-propyl)phenol released after 0.5 hours,
   5 to 50% by weight 3-(3-dimethylaminol-ethyl-2-methyl-propyl)phenol released after 1 hour,
   10 to 75% by weight 3-(3-dimethylamino-1-ethyl-2-methyl-propyl)phenol released after 2 hours,
   15 to 82% by weight 3-(3-dimethylamino-1-ethyl-2-methyl-propyl)phenol released after 3 hours,
   30 to 97% by weight 3-(3-dimethylamino-1-ethyl-2-methyl-propyl)phenol released after 6 hours,
   more than 50% by weight 3-(3-dimethylamino-1-ethyl-2-methyl-propyl)phenol released after 12 hours,
   more than 70% by weight 3-(3-dimethylamino-1-ethyl-2-methyl-propyl)phenol released after 18 hours, and
   more than 80% by weight 3-(3-dimethylamino-1-ethyl-2-methyl-propyl)phenol released after 24 hours,
   wherein a peak plasma level of the active ingredient is obtained in vivo, according to the plasma concentration/time graph, of between about 2 to about 10 hours after administration of the formulation, and the matrix forming agents have a viscosity of 3,000 to 150,000 mPas in a 2% by weight solution at 20° C.

2. A pharmaceutical formulation according to claim 1, wherein the matrix forming agents have a viscosity of 10,000 to 150,000 mPa·s in a 2% by weight solution at 20° C.

3. A pharmaceutical formulation according to claim 1, wherein the matrix forming agents have a viscosity of 50,000 to 150,000 mPa·s in a 2% by weight solution at 20° C.

4. A pharmaceutical formulation according to claim 1, wherein the matrix forming agent comprises at least one substance selected from the group consisting of hydroxypropylmethyl celluloses, hydroxyethyl celluloses, and hydroxypropyl celluloses.

5. A pharmaceutical formulation according to claim 1, wherein said formulation contains from 0.5 to 85% by weight active ingredient and from 8 to 40% by weight matrix forming agents.

6. A pharmaceutical formulation according to claim 1, wherein said formulation comprises from 3 to 70% by weight active ingredient and from 10 to 35% by weight matrix forming agents.

7. A pharmaceutical formulation according to claim 6, wherein said formulation comprises from 8 to 66% by weight active ingredient and from 10 to 30% by weight matrix forming agents.

8. A pharmaceutical formulation according to claim 1, wherein the peak plasma level of the active ingredient is obtained in vivo 3.5 to 6 hours after administration of the formulation.

9. A pharmaceutical formulation according to claim 1, wherein the active ingredient comprises (+)-(1S,2S)-3-(3-dimethylamino-1-ethyl-2-methyl-propyl)phenol or a pharmaceutically acceptable salt thereof.

10. A pharmaceutical formulation according to claim 1, wherein the active ingredient comprises (−)-(1R,2R)-3-(3-dimethylamino-1-ethyl-2-methyl-propyl)phenol or a pharmaceutically acceptable salt thereof.

11. A tablet for twice daily oral administration of 3-(3-dimethylamino-1-ethyl-2-methyl-propyl)phenol, said tablet containing a pharmaceutical formulation according to claim 1.

12. A slow-release oral pharmaceutical formulation comprising 3-(3-dimethylamino-1-ethyl-2-methyl-propyl)phenol or a pharmaceutically acceptable salt thereof as active ingredient in a matrix, wherein the matrix comprises 1 to 40% by weight of one or more pharmaceutically matrix forming agents selected from the group consisting of hydroxypropylmethyl celluloses (HPMC), hydroxyethyl celluloses, hydroxypropyl celluloses (HPC), methyl celluloses, ethyl celluloses and carboxymethyl celluloses, wherein a peak plasma level of the active ingredient is obtained in vivo, according to the plasma concentration/time graph, of between about 2 to about 10 hours after administration of the formulation, and the matrix forming agents have a viscosity of 3,000 to 150,000 mPa·s in a 2% by weight aqueous solution at 20° C.

13. A pharmaceutical formulation according to claim 12, wherein the matrix forming agents have a viscosity of 10,000 to 150,000 mPa·s in a 2% by weight solution at 20° C.

14. A pharmaceutical formulation according to claim 12, wherein the matrix forming agents have a viscosity of 50,000 to 150,000 mPa·s in a 2% by weight solution at 20° C.

15. A pharmaceutical formulation according to claim 12, wherein the matrix forming agent comprises at least one substance selected from the group consisting of hydroxypropylmethyl celluloses, hydroxyethyl celluloses, and hydroxypropyl celluloses.

16. A pharmaceutical formulation according to claim 12, wherein said formulation contains from 0.5 to 85% by weight active ingredient and from 8 to 40% by weight matrix forming agents.

17. A pharmaceutical formulation according to claim 12, wherein said formulation comprises from 3 to 70% by weight active ingredient and from 10 to 35% by weight matrix forming agents.

18. A pharmaceutical formulation according to claim 17, wherein said formulation comprises from 8 to 66% by weight active ingredient and from 10 to 30% by weight matrix forming agents.

19. A pharmaceutical formulation according to claim 12, wherein the peak plasma level of the active ingredient is obtained in vivo 3.5 to 6 hours after administration of the formulation.

20. A pharmaceutical formulation according to claim 12, wherein the active ingredient comprises (+)-(1S, 2 S)-3-(3-dimethylamino-1-ethyl-2-methyl-propyl)phenol or a pharmaceutically acceptable salt thereof.

21. A pharmaceutical formulation according to claim 12, wherein the active ingredient comprises (−)-(1R,2R)-3-(3-dimethyl amino-1-ethyl-2-methyl-propyl)phenol or a pharmaceutically acceptable salt thereof.

22. A tablet for twice daily oral administration of 3-(3-dimethylamino-1-ethyl-2-methyl-propyl)phenol, said tablet containing a pharmaceutical formulation according to claim 12.

23. A method of treating pain in a patient in need thereof comprising administering to said patient twice daily a tablet according to claim 11.

24. A method of treating pain in a patient in need thereof comprising administering to said patient twice daily a tablet according to claim 22.

25. A pharmaceutical formulation according to claim 1, wherein the matrix forming agent is hydroxypropylmethylcellulose having a viscosity of ca. 100,000 mPa·s in a 2 wt % solution at 20° C.

26. A pharmaceutical formulation according to claim 12, wherein the matrix forming agent is hydroxypropylmethylcellulose having a viscosity of ca. 100,000 mPa·s in a 2 wt % solution at 20° C.

* * * * *